United States Patent
Matsuda et al.

(10) Patent No.: US 7,572,940 B2
(45) Date of Patent: Aug. 11, 2009

(54) PROCESS FOR PRODUCING 2-PERFLUOROALKYLETHYL ALCOHOL

(75) Inventors: Yuuki Matsuda, Settsu-Shi (JP); Takeomi Hirasaka, Settsu-Shi (JP); Takuya Ichida, Settsu-Shi (JP)

(73) Assignee: Daikin Industries, Ltd., Osaka-shi (JP)

( * ) Notice: Subject to any disclaimer, the term of this patent is extended or adjusted under 35 U.S.C. 154(b) by 0 days.

(21) Appl. No.: 12/258,197

(22) Filed: Oct. 24, 2008

(65) Prior Publication Data

US 2009/0118552 A1  May 7, 2009

(30) Foreign Application Priority Data

Oct. 24, 2007  (JP) .................. P2007-276069

(51) Int. Cl.
*C07C 29/09* (2006.01)
*C07C 29/12* (2006.01)

(52) U.S. Cl. .................................... 568/842

(58) Field of Classification Search .................. 568/842
See application file for complete search history.

(56) References Cited

U.S. PATENT DOCUMENTS

| 3,283,012 A | 11/1966 | Day |
| 5,202,506 A | 4/1993 | Kirchner et al. |

FOREIGN PATENT DOCUMENTS

| JP | 40-19085 | 8/1940 |
| JP | 5-507269 A | 10/1993 |
| JP | 3438905 B2 | 6/2003 |
| WO | WO-91/18857 A1 | 12/1991 |

*Primary Examiner*—Elvis O Price
(74) *Attorney, Agent, or Firm*—Birch, Stewart, Kolasch & Birch, LLP

(57) ABSTRACT

In a first sulfation step, 2-perfluoroalkylethyl iodide is brought into contact with fuming sulfuric acid to obtain a reaction mixture comprising 2-perfluoroalkylethyl sulfate and bis(2-perfluoroalkylethyl)sulfate. Then, in a first hydrolysis step, 2-perfluoroalkylethyl sulfate produced in the first sulfation step is hydrolyzed to obtain a reaction mixture comprising 2-perfluoroalkylethyl alcohol. In a second sulfation step, bis(2-perfluoroalkylethyl)sulfate produced in the first sulfation step is brought into contact with fuming sulfuric acid to obtain a reaction mixture comprising 2-perfluoroalkylethyl sulfate. Then, in a second hydrolysis step, 2-perfluoroalkylethyl sulfate produced in the second sulfation step is hydrolyzed to obtain a reaction mixture comprising 2-perfluoroalkylethyl alcohol. According to such procedures, 2-perfluoroalkylethyl alcohol can be obtained in a high yield.

6 Claims, 3 Drawing Sheets

US 7,572,940 B2

1

PROCESS FOR PRODUCING 2-PERFLUOROALKYLETHYL ALCOHOL

CROSS-REFERENCE TO RELATED APPLICATIONS

The present application claims priority under 35 U.S.C. §119 to Japanese Patent Application No. 2007-276069 filed on Oct. 24, 2007, entitled "PROCESS FOR PRODUCING 2-PERFLUOROALKYLETHYL ALCOHOL". The contents of that application are incorporated herein by reference thereto in their entirety.

BACKGROUND OF THE INVENTION

1. Field of the Invention

The present invention relates to a process for producing 2-perfluoroalkylethyl alcohol, and more particularly to a process of obtaining 2-perfluoroalkylethyl alcohol by sulfation and subsequent hydrolysis using 2-perfluoroalkylethyl iodide and bis(2-perfluoroalkylethyl)sulfate.

2. Description of Related Art 2-perfluoroalkylethyl alcohol is used as an intermediate for the production of substances useful for water- and oil-repellent, surfactants, mold release agents and so on.

There is generally known, as a process for producing 2-perfluoroalkylethyl alcohol, a process of sulfonating 2-perfluoroalkylethyl iodide with fuming sulfuric acid to produce 2-perfluoroalkylethyl sulfate and hydrolyzing 2-perfluoroalkylethyl sulfate to obtain 2-perfluoroalkylethyl alcohol (refer to Japanese Examined Patent Publication (Kokoku) No. 40-19085 and Published Japanese Translation No. 5-507269 of the PCT Application).

With reference to Japanese Examined Patent Publication (Kokoku) No. 40-19085, it is understood that such a conventional production process is composed of two reactions which are sequentially executed. A first reaction is a sulfation reaction of reacting 2-perfluoroalkylethyl iodide represented by RfCH$_2$CH$_2$I with fuming sulfuric acid to produce 2-perfluoroalkylethyl sulfate (fluoroalkyl hydrogen sulfate), represented by RfCH$_2$CH$_2$OSO$_2$OH, and I$_2$. A second reaction is a hydrolysis reaction of hydrolyzing 2-perfluoroalkylethyl sulfate produced in the first reaction with an aqueous acid to produce 2-perfluoroalkylethyl alcohol, represented by RfCH$_2$CH$_2$OH, and sulfuric acid.

In the above conventional production process, bis(2-perfluoroalkylethyl)sulfate and an iodide (2-perfluoroalkylethyl iodide, the same shall apply hereinafter) are produced as by-products and a yield of 2-perfluoroalkylethyl alcohol (RfCH$_2$CH$_2$OH) as the target substance contained in a final reaction mixture (final mixture) which also contains the by-products is about 80% at most. A main by-product is bis(2-perfluoroalkylethyl)sulfate and an amount of the iodide in the final mixture is as small as about several % by weight which amount is determined by a gas chromatographic analysis. It is necessary to decrease an amount of the by-product contained in the final mixture, particularly bis(2-perfluoroalkylethyl)sulfate so as to attain a high yield.

Bis(2-perfluoroalkylethyl)sulfate is a by-product in the above first reaction (sulfation reaction). Although it is known that bis(2-perfluoroalkylethyl)sulfate is hydrolyzed to produce 2-perfluoroalkylethyl alcohol as the target substance (refer to Japanese Examined Patent Publication (Kokoku) No. 40-19085), more time and more severe acidic conditions than those of hydrolysis of 2-perfluoroalkylethyl sulfate, are required and therefore it is difficult to hydrolyze bis(2-perfluoroalkylethyl)sulfate to produce 2-perfluoroalkylethyl

2 alcohol in the above second reaction. When the second reaction is carried out under severe conditions where bis(2-perfluoroalkylethyl)sulfate is also hydrolyzed, an ether represented by RfCH$_2$CH$_2$OCH$_2$CH$_2$Rf is produced as a by-product by a side reaction between bis(2-perfluoroalkylethyl)sulfate and 2-perfluoroalkylethyl alcohol.

Bis(2-perfluoroalkylethyl)sulfate can also be hydrolyzed under alkali conditions after being isolated (refer to Japanese Examined Patent Publication (Kokoku) No. 40-19085). In the reaction, an olefin represented by RfCH=CH$_2$ is produced as a by-product by a desulphation reaction of bis(2-perfluoroalkylethyl)sulfate.

As described above, a method of reducing an amount of bis(2-perfluoroalkylethyl)sulfate that is produced as a by-product in the above first reaction (sulfation reaction) and contained in the final mixture, which method includes hydrolyzing bis(2-perfluoroalkylethyl)sulfate, has disadvantages associated with by-products such as ether or olefin, and the reaction time.

In the above first reaction, by using fuming sulfuric acid in a large excess amount based on 2-perfluoroalkylethyl iodide as a raw material, an amount of bis(2-perfluoroalkylethyl)sulfate produced as a by-product can also be decreased. However, considering the reactor size, the amount of fuming sulfuric acid to be used, and the amount of waste water produced by neutralization and dilution, this method is inefficient and is not suited for industrial production.

As an improvement of a conventional production process, the addition of an oxidizing agent in a hydrolysis step is proposed so as to decrease an amount of iodide contained in the final product (refer to Japanese Patent No. 3,438,905). However, the addition of the oxidizing agent in the hydrolysis step in this improved process does not always sufficiently suppress the production of the by-product iodide. Furthermore in this improved process, the production of the by-product bis(2-perfluoroalkylethyl)sulfate is not taken into consideration at all. As described above, since the amount of iodide contained in the final mixture is as small as about several % by weight even in the case of a conventional production process, the yield of 2-perfluoroalkylethyl alcohol cannot be effectively increased by this improved process.

SUMMARY OF THE INVENTION

A main object of the present invention is to provide a process for producing 2-perfluoroalkylethyl alcohol in a high yield.

The present inventors have intensively studied and found that 2-perfluoroalkylethyl alcohol can be obtained finally in a high yield by subjecting bis(2-perfluoroalkylethyl)sulfate, produced as a by-product, to a sulfation reaction with fuming sulfuric acid, and thus completed the present invention.

The present invention provides a process for producing 2-perfluoroalkylethyl alcohol, which includes:

a first sulfation step of bringing 2-perfluoroalkylethyl iodide represented by the following formula:

(wherein Rf is a linear perfluoroalkyl group having 1 to 10 carbon atoms, this definition of Rf is also applied to formulas herein below unless otherwise defined), into contact with fuming sulfuric acid to obtain a first sulfation reaction mixture including (thus produced) 2-perfluoroalkylethyl sulfate represented by the following formula:

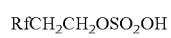

and bis(2-perfluoroalkylethyl)sulfate as a by-product represented by the following formula:

$Rf^1CH_2CH_2OSO_2OCH_2CH_2Rf^2$ (wherein $Rf^1$ and $Rf^2$ are a linear perfluoroalkyl group having 1 to 10 carbon atoms which may be the same or different from each other, this definition of $Rf^1$ and $Rf^2$ is also applied to formulas herein below unless otherwise defined);

a first hydrolysis step of hydrolyzing 2-perfluoroalkylethyl sulfate produced in the first sulfation step to obtain a first hydrolysis reaction mixture including (thus produced) 2-perfluoroalkylethyl alcohol represented by the following formula:

$RfCH_2CH_2OH$;

a second sulfation step of bringing bis(2-perfluoroalkylethyl)sulfate produced in the first sulfation step into contact with fuming sulfuric acid to obtain a second sulfation reaction mixture including (thus produced) 2-perfluoroalkylethyl sulfate represented by the following formulas:

$Rf^1CH_2CH_2OSO_2OH$ and $Rf^2CH_2CH_2OSO_2OH$; and a second hydrolysis step of hydrolyzing 2-perfluoroalkylethyl sulfate produced in the second sulfation step to obtain a second hydrolysis reaction mixture including (thus produced) 2-perfluoroalkylethyl alcohol represented by the following formulas:

$Rf^1CH_2CH_2OH$ and $Rf^2CH_2CH_2OH$;

wherein the first and the second sulfation steps are separate steps (in other words, conducted separately) from each other, and the first and the second hydrolysis steps are separate steps from each other.

In the present invention, the "reaction mixture" means a mixture obtained through a reaction and includes not only a reaction product, but also an unreacted raw material. The reaction mixture can be in any state, for example, a state where an organic substance and an inorganic substance are mixed, and a state where the mixture is separated into an organic phase and an inorganic phase. When the "reaction mixture" is used, the entire reaction mixture may be used, or a portion thereof (for example, only the organic phase) may be used.

It should be noted that the finally obtained 2-perfluoroalkylethyl alcohol is represented by $RfCH_2CH_2OH$, $Rf^1CH_2CH_2OH$ and $Rf^2CH_2CH_2OH$, and both $RfCH_2CH_2OH$ and $Rf^2CH_2CH_2OH$ are generalized down to the formula $RfCH_2CH_2OH$.

In the production process of the present invention, since bis(2-perfluoroalkylethyl)sulfate produced as a byproduct in the first sulfation step is converted into 2-perfluoroalkylethyl sulfate in the second sulfation step and then 2-perfluoroalkyl sulfate is converted into 2-perfluoroalkylethyl alcohol in the second hydrolysis step, the amount of bis(2-perfluoroalkylethyl)sulfate contained in the finally obtained reaction mixture can be decreased and therefore the amount of 2-perfluoroalkylethyl alcohol as the target substance can be increased by just that much. Since bis(2-perfluoroalkylethyl)sulfate is a main by-product in a conventional production process, the yield of 2-perfluoroalkylethyl alcohol as the target substance can be effectively increased by the production process of the present invention.

While the present invention is not intended to be bound by any specific theory, the reason why the reaction proceeds in the second sulfation step is considered to be as follows. In the presence of 2-perfluoroalkylethyl iodide, sulfur trioxide is used more easily in the reaction of producing 2-perfluoroalkylethyl sulfate from 2-perfluoroalkylethyl iodide than in the reaction of producing 2-perfluoroalkylethyl sulfate from bis(2-perfluoroalkylethyl)sulfate, and therefore the latter reaction preferentially proceeds. Therefore, when 2-perfluoroalkylethyl iodide as a raw material is sulfated in the first sulfation step, the latter reaction preferentially proceeds and the former reaction does not proceed too much and thus the resultant first sulfation reaction mixture contains bis(2-perfluoroalkylethyl)sulfate. However, as in the production process of the present invention, when the second sulfation step is provided in addition to the first sulfation step and sulfation is carried out in the second sulfation step in a state where 2-perfluoroalkylethyl iodide exists in a comparatively small amount, the former reaction proceeds and thus bis(2-perfluoroalkylethyl)sulfate can be converted into 2-perfluoroalkylethyl sulfate.

The first hydrolysis step and the second hydrolysis step in the production process of the present invention can be carried out under mild conditions when compared with severe acidic conditions required so as to directly hydrolyze bis(2-perfluoroalkylethyl)sulfate to produce 2-perfluoroalkylethyl alcohol. Therefore, it is possible to avoid the production of the ether as a by-product which can be caused under the severe conditions where bis(2-perfluoroalkylethyl)sulfate is also hydrolyzed.

In the production process of the present invention, since it is not necessary to carry out the first hydrolysis step and the second hydrolysis step under alkaline conditions, it is possible to avoid the production of the olefin as a by-product which can be caused when hydrolysis is carried out under the alkaline conditions after bis(2-perfluoroalkylethyl)sulfate has been isolated.

Furthermore, in the production process of the present invention, it is not necessary to decrease the amount of bis(2-perfluoroalkylethyl)sulfate produced as a by-product in the first sulfation step when compared with the prior art, and the amount may be more than that in case of the prior art. Therefore, the amount of fuming sulfuric acid, more specifically sulfur trioxide is not necessary to be large excess relative to 2-perfluoroalkylethyl iodide in the first sulfation step, and the amount may be less than that in case of the prior art. For example, the fuming sulfuric acid used in the first sulfation step may contain sulfur trioxide of which molar ratio to that of 2-perfluoroalkylethyl iodide is not greater than three. Therefore, the production process of the present invention is advantageous for industrial production in view of the reactor size, the amount of fuming sulfuric acid to be used, and the amount of waste water.

In one aspect of the present invention, the production process of the present invention can be carried out as in the following manner:

the first sulfation reaction mixture including 2-perfluoroalkylethyl sulfate and bis(2-perfluoroalkylethyl)sulfate is used in the first hydrolysis step to obtain the first hydrolysis reaction mixture including 2-perfluoroalkylethyl alcohol and (further including) bis(2-perfluoroalkylethyl)sulfate;

this first hydrolysis reaction mixture is used in the second sulfation step to obtain the second sulfation reaction mixture (further) including 2-perfluoroalkylethyl alcohol and (or in addition to) 2-perfluoroalkylethyl sulfate; and this second sulfation reaction mixture is used in the second hydrolysis step to obtain the second hydrolysis reaction mixture including 2-perfluoroalkylethyl alcohol.

In this aspect, the finally obtained reaction mixture is the second hydrolysis reaction mixture, and the yield is determined by analyzing the second hydrolysis reaction mixture.

In another aspect of the present invention, the production process of the present invention can be carried out as in the following manner:

the first sulfation reaction mixture including 2-perfluoroalkylethyl sulfate and bis(2-perfluoroalkylethyl)sulfate is used in the first hydrolysis step to obtain the first hydrolysis reaction mixture including 2-perfluoroalkylethyl alcohol and (further including) bis(2-perfluoroalkylethyl)sulfate;

this first hydrolysis reaction mixture is separated into a fraction of 2-perfluoroalkylethyl alcohol and a fraction of bis(2-perfluoroalkylethyl)sulfate;

thus separated fraction of bis(2-perfluoroalkylethyl)sulfate is used in the second sulfation step to obtain the second sulfation reaction mixture including 2-perfluoroalkylethyl sulfate; and this second sulfation reaction mixture is used in the second hydrolysis step to obtain the second hydrolysis reaction mixture including 2-perfluoroalkylethyl alcohol.

In this aspect, the finally obtained reaction mixture is a sum of the fraction of 2-perfluoroalkylethyl alcohol and the second hydrolysis reaction mixture, and the yield can be determined by analyzing them individually or analyzing the sum of them.

However, the present invention is not limited to these aspects. For example, it is considered that the production process of the present invention can also be carried out as in the following manner:

the first sulfation reaction mixture is separated into a fraction of 2-perfluoroalkylethyl sulfate and a fraction of bis(2-perfluoroalkylethyl) sulfate;

the fraction of 2-perfluoroalkylethyl sulfate separated from the first sulfation reaction mixture is used in the first hydrolysis step to obtain the first hydrolysis reaction mixture including 2-perfluoroalkylethyl alcohol;

the fraction of bis(2-perfluoroalkylethyl)sulfate separated from the first sulfation reaction mixture is used in the second sulfation step to obtain the second sulfation reaction mixture including 2-perfluoroalkylethyl sulfate; and the second sulfation reaction mixture is used in the second hydrolysis step to obtain the second hydrolysis reaction mixture including 2-perfluoroalkylethyl alcohol.

According to the present invention, the final yield of 2-perfluoroalkylethyl alcohol can be effectively increased since bis(2-perfluoroalkylethyl)sulfate produced as a by-product in the first sulfation step is converted into 2-perfluoroalkylethyl sulfate in the second sulfation step, and then converted into 2-perfluoroalkylethyl alcohol in the second hydrolysis step.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF THE PREFERRED EMBODIMENTS

Figure 1:
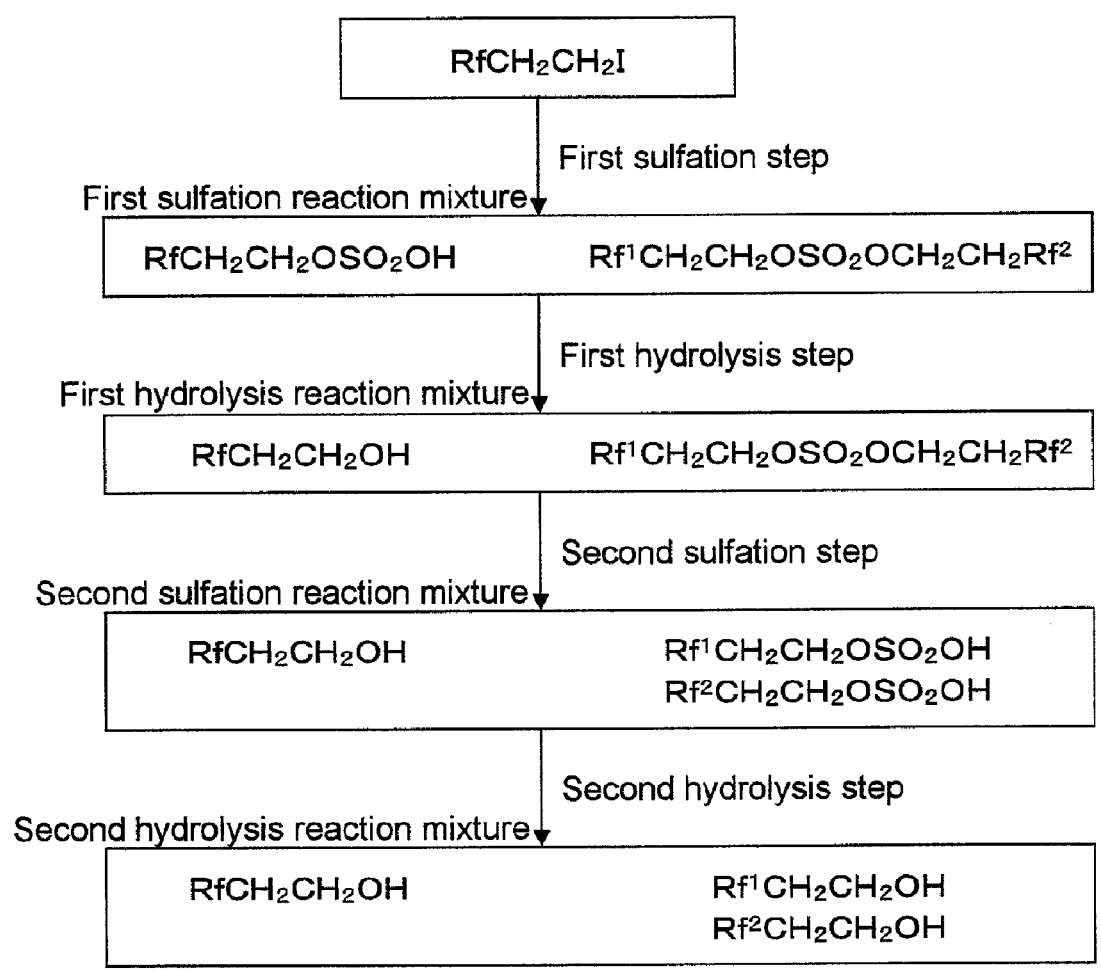
FIG. 1 is a flow chart for showing a process for producing 2-perfluoroalkylethyl alcohol according to one embodiment of the present invention.

The process for producing 2-perfluoroalkylethyl alcohol in one embodiment of the present invention will be described below with reference to FIG. 1.

First Sulfation Step

First, 2-perfluoroalkylethyl iodide is sulfated by bringing it into contact with fuming sulfuric acid. Fuming sulfuric acid and 2-perfluoroalkylethyl iodide are sequentially charged into a reactor such as autoclave and they are brought into contact with each other under proper reaction conditions thereby allowing a sulfation reaction to proceed.

2-perfluoroalkylethyl iodide as a raw material is represented by the following formula:

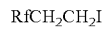

wherein Rf is a linear perfluoroalkyl group having 1 to 10 carbon atoms. More specifically, Rf may be represented by $F(CF_2)_n—$ (wherein "n" is an integer of 1 to 10).

In this step, fuming sulfuric acid to be used for sulfation in this step contains concentrated sulfuric acid and sulfur trioxide, as is generally known. Fuming sulfuric acid to be used may have any proper concentration of sulfur trioxide, and can be appropriately selected in consideration of availability and handling properties.

When the reaction temperature and pressure are a temperature and pressure at which 2-perfluoroalkylethyl iodide and fuming sulfuric acid are in a liquid state, a sulfation reaction of 2-perfluoroalkylethyl iodide proceeds. Under a normal pressure, the temperature can be adjusted within a range from about 0 to about 90° C. The reaction time is not particularly limited and can be adjusted, for example, within a range from about 1 to about 2 hours.

2-perfluoroalkylethyl sulfate is produced by the sulfation reaction and is represented by the following formula:

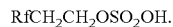

During the sulfation, bis(2-perfluoroalkylethyl)sulfate is produced as a by-product and is represented by the following formula:

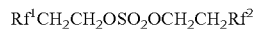

wherein $Rf^1$ and $Rf^2$ are a linear perfluoroalkyl group having 1 to 10 carbon atoms which may be the same or different from each other. More specifically, $Rf^1$ and $Rf^2$ each may be represented by $F(CF_2)_m—$ and $—(CF_2)_l F$ (wherein "m" and "l" are an integer of 1 to 10 which may be the same or different from each other).

As a result, a first sulfation reaction mixture containing 2-perfluoroalkylethyl sulfate and bis(2-perfluoroalkylethyl) sulfate is obtained. The first sulfation reaction mixture further contains unreacted fuming sulfuric acid and is usually obtained in a state where an organic substance and an inorganic substance are mixed.

The amount of bis(2-perfluoroalkylethyl)sulfate contained in the first sulfation reaction mixture can vary depending on the order in which or the proportion at which of 2-perfluoroalkylethyl iodide and fuming sulfuric acid is charged to the reactor. In a conventional production process, it was considered to be preferred that fuming sulfuric acid is charged to the reactor first and then 2-perfluoroalkylethyl iodide is charged, and also fuming sulfuric acid is used in an excess amount based on 2-perfluoroalkylethyl iodide so that the amount of bis(2-perfluoroalkylethyl)sulfate is as small as possible. However, in the present invention, there is not such a restriction since it is not necessary to decrease the amount of bis(2-perfluoroalkylethyl)sulfate produced, as a by-product, in the first sulfation step.

Therefore, in this step, the order in which 2-perfluoroalkylethyl iodide and fuming sulfuric acid is charged to the reactor is not particularly limited and either of them may be charged first.

The ratio of the amount of 2-perfluoroalkylethyl iodide to that of fuming sulfuric acid to be used in this step is not particularly limited. In consideration of costs and efficiency, a molar ratio of sulfur trioxide in fuming sulfuric acid to 2-perfluoroalkylethyl iodide is preferably from about 0.1 to about 11, and more preferably from 0.5 to 7. However, the molar ratio of sulfur trioxide in fuming sulfuric acid to 2-perfluoroalkylethyl iodide may not be greater than 3. On the other hand, a molar ratio of sulfuric acid in fuming sulfuric acid to 2-perfluoroalkylethyl iodide as a raw material is preferably from about 1 to about 50, and more preferably from about 10 to about 40.

First Hydrolysis Step

Next, 2-perfluoroalkylethyl sulfate produced in the first sulfation step is hydrolyzed. The first sulfation reaction mixture, generally the entire mixture obtained in the previous step is charged as it is, to water or an aqueous sodium sulfite solution charged preliminarily in the reactor, followed by bringing it into contact with 2-perfluoroalkylethyl sulfate under proper reaction conditions, thereby allowing a hydrolysis reaction to proceed. When a temperature-controllable reactor is used, the order of charging water or the aqueous sodium sulfite solution and the first sulfation reaction mixture may be reversed.

The amount of water to be used for hydrolysis may be an amount sufficient to consume 2-perfluoroalkylethyl sulfate during the hydrolysis reaction in this step and to convert unreacted sulfur trioxide of fuming sulfuric acid used in the first sulfation step into sulfuric acid. Since only 2-perfluoroalkylethyl sulfate has to be hydrolyzed in this step, it is not necessary to expose an aqueous phase to severe acidic conditions or alkali conditions.

The reaction temperature and pressure are preferably adjusted to the temperature and pressure where a hydrate gel of 2-perfluoroalkylethyl alcohol is not formed when 2-perfluoroalkylethyl sulfate is hydrolyzed. Under a normal pressure, the temperature is preferably adjusted to about 80° C. or higher. It is not essential to avoid formation of the hydrate gel, and the alcohol hydrate gel thus formed can be converted into 2-perfluoroalkylethyl alcohol by heating (for example, heating to about 80° C. or higher under a normal pressure). The reaction time is not particularly limited and can be adjusted, for example, within a range from about 0.5 to about 2 hours.

2-perfluoroalkylethyl alcohol as the target substance is produced by the hydrolysis reaction and is represented by the following formula:

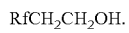

During the hydrolysis reaction, bis(2-perfluoroalkylethyl)sulfate contained in the first sulfation reaction mixture is substantially maintained as it is. Since the hydrolysis reaction can be carried out under mild reaction conditions, by-products such as iodide or ether are scarcely produced.

As a result, a first hydrolysis reaction mixture containing 2-perfluoroalkylethyl alcohol and 2-perfluoroalkylethyl sulfate can be obtained. The first hydrolysis reaction mixture further contains unreacted water and is usually obtained in a state where an organic substance and an inorganic substance are mixed. It is preferred that the first hydrolysis reaction mixture is separated into an organic phase and an aqueous phase and then the organic phase is isolated and used in the following step.

Second Sulfation Step

Next, bis(2-perfluoroalkylethyl)sulfate produced in the first sulfation step and maintained in the first hydrolysis reaction mixture is sulfated by bringing it in contact with fuming sulfuric acid. To a reactor such as autoclave, fuming sulfuric acid and the first hydrolysis reaction mixture (more specifically, the organic phase separated in the above step) are sequentially charged and are brought into contact with each other under proper reaction conditions thereby allowing a sulfation reaction to proceed. The order of charging the fuming sulfuric acid and the first hydrolysis reaction mixture (more specifically, the organic phase) to the reactor is not particularly limited and either of them may be charged first.

Fuming sulfuric acid to be used for sulfation in this step may have any proper concentration of sulfur trioxide similar to that used in the first sulfation step, and can be appropriately selected in consideration of availability and handling properties.

Under a normal pressure, the temperature must be adjusted within a range from about 50 to about 80° C. so as to allow the sulfation reaction of bis(2-perfluoroalkylethyl)sulfate to proceed. The reaction time is not particularly limited and varies depending on conditions such as temperature, and can be adjusted, for example, within a range from about 1 to about 2 hours.

The ratio of the amount of fuming sulfuric acid to that of bis(2-perfluoroalkylethyl)sulfate in this step is not particularly limited. In consideration of costs and efficiency, a molar ratio of sulfur trioxide in fuming sulfuric acid to bis(2-perfluoroalkylethyl)sulfate is preferably from about 0.1 to about 11, and more preferably from about 0.5 to about 7 mol. A molar ratio of sulfuric acid in fuming sulfuric acid to bis(2-perfluoroalkylethyl)sulfate is preferably from about 1 to about 50, and more preferably from about 10 to about 40.

The sulfation reaction gives 2-perfluoroalkylethyl sulfate represented by the following formulas:

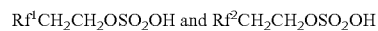

and these formulas can be generalized by the following formula:

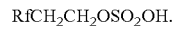

During the sulfation reaction, 2-perfluoroalkylethyl alcohol contained in the first hydrolysis reaction mixture is substantially maintained as it is.

Although the first hydrolysis reaction mixture used in this step can contain unreacted 2-perfluoroalkylethyl iodide, sulfation of bis(2-perfluoroalkylethyl)sulfate proceeds efficiently. This is because an amount of 2-perfluoroalkylethyl iodide contained in the mixture is small.

As a result, a second sulfation reaction mixture containing 2-perfluoroalkylethyl alcohol and 2-perfluoroalkylethyl sulfate can be obtained. The second sulfation reaction mixture further contains unreacted fuming sulfuric acid and is usually obtained in a state where an organic substance and an inorganic substance are mixed.

Second Hydrolysis Step

Next, 2-perfluoroalkylethyl sulfate produced in the second sulfation step is hydrolyzed. The operation procedure and reaction conditions in this step can be the same as those described above with respect to the first hydrolysis step unless otherwise specified.

2-perfluoroalkylethyl alcohol as the target substance is produced by the hydrolysis reaction and is represented by the following formulas:

$Rf^1CH_2CH_2OH$ and $Rf^2CH_2CH_2OH$ and these formulas can be generalized by the following formula:

$RfCH_2CH_2OH$.

During the hydrolysis reaction, 2-perfluoroalkylethyl alcohol contained originally in the second sulfation reaction mixture is substantially maintained as it is.

As a result, a second hydrolysis reaction mixture containing 2-perfluoroalkylethyl alcohol can be obtained. The second hydrolysis reaction mixture further contains unreacted water and is usually obtained in a state where an organic substance and an inorganic substance are mixed. 2-perfluoroalkylethyl alcohol as the target substance can be recovered by separating the second hydrolysis reaction mixture into an organic phase and an aqueous phase and fractionating the organic phase.

The process for producing 2-perfluoroalkylethyl alcohol in one embodiment of the present invention (FIG. 1) has been described above. The present invention can be carried out in another embodiment.

Figure 2:
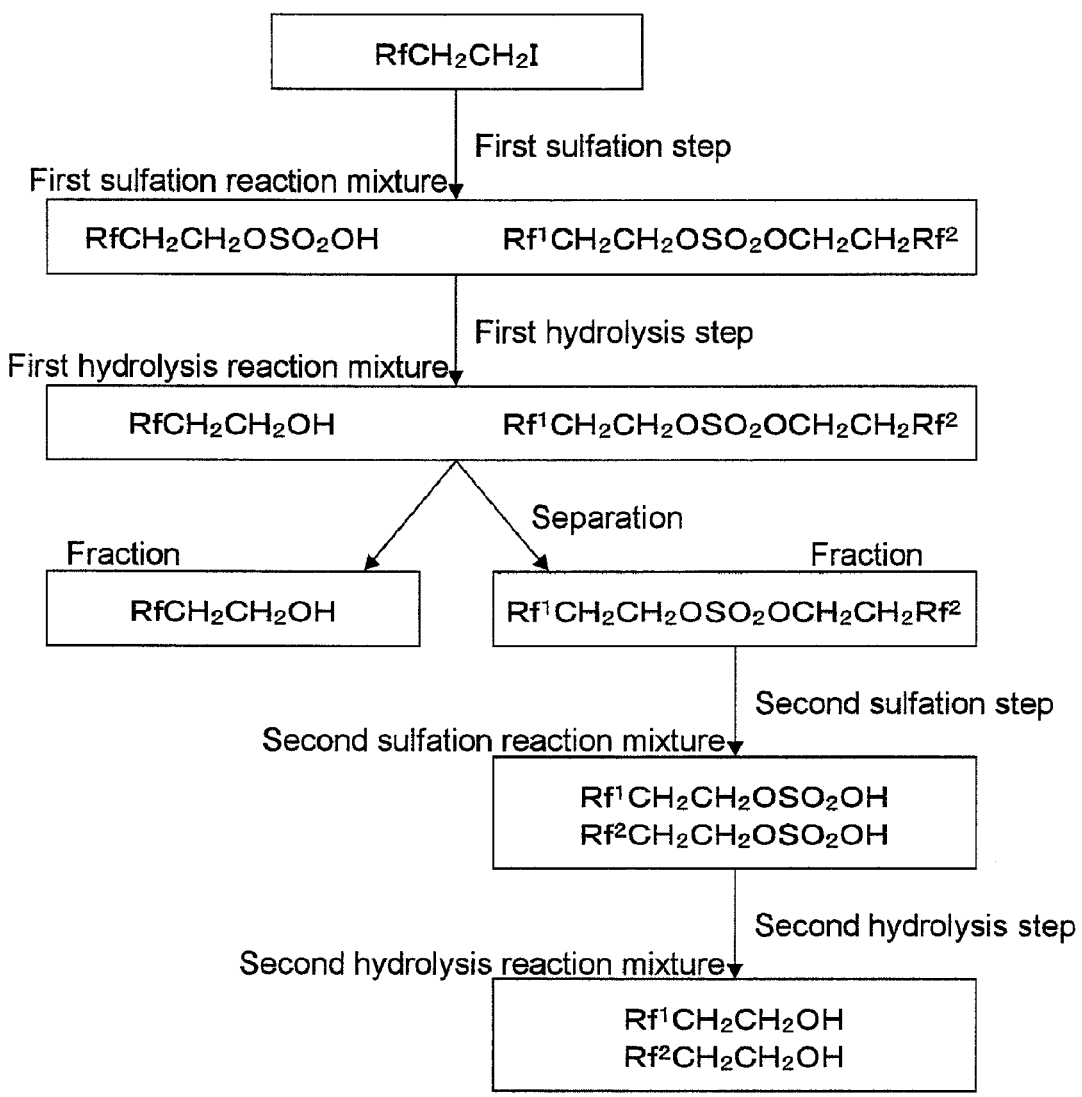
FIG. 2 is a flow chart for showing a process for producing 2-perfluoroalkylethyl alcohol according to another embodiment of the present invention.

The another embodiment of the present invention is described below, with reference to FIG. 2. In this embodiment, a first hydrolysis reaction mixture containing 2-perfluoroalkylethyl alcohol and 2-perfluoroalkylethyl sulfate obtained in a first hydrolysis step is separated into an organic phase and an inorganic phase (an aqueous phase), and the organic phase is fractionated. The resultant organic phase is subjected to a rectification operation thereby being separated into a fraction of 2-perfluoroalkylethyl alcohol and a fraction of 2-perfluoroalkylethyl sulfate, and the latter fraction is subjected to a second sulfation step and a second hydrolysis step. In this embodiment, 2-perfluoroalkylethyl alcohol can be recovered as a fraction of 2-perfluoroalkylethyl alcohol and a second hydrolysis reaction mixture. The other operation procedure and the other reaction conditions in each step in this embodiment can be the same as those in the previous embodiment described with reference to FIG. 1.

When the second hydrolysis reaction mixture contains bis(2-perfluoroalkylethyl)sulfate and it is required to further improve the yield, the same steps as the second sulfation step and the second hydrolysis step may be repeatedly carried out (not shown) after the second hydrolysis step.

EXAMPLES

The following tests were carried out so as to confirm the effect of the present invention.

(Test 1)

Sulfation Step

In a 500 ml four-necked flask, 35.13 g fuming sulfuric acid containing 20% by weight of sulfur trioxide and 1.32 g water were supplied to prepare 36.45 g fuming sulfuric acid containing 3.3% by weight of sulfur trioxide. While stirring with a temperature maintained in the flask at 30° C., 14.49 g $C_6F_{13}C_2H_4I$ was added dropwise over 40 minutes and then stirring was continued for one hour.

Hydrolysis Step

While cooling the flask in an ice bath, 160.71 g of a 1.5 wt % aqueous sodium sulfite solution was added dropwise over one hour, and then the mixture was heated to 80° C. and maintained at the temperature for one hour. The reaction solution was allowed to stand, thereby being separated into an organic phase and an inorganic phase, 10.39 g organic phase as a lower phase was fractionated. The organic phase was analyzed. The results are shown in the following table. Analysis was carried out by gas chromatography in this test, as well as in the following tests.

TABLE 1

| | |
|---|---|
| $C_6F_{13}C_2H_4OH$ | 88.19% by weight (yield 82.3%) |
| $C_6F_{13}C_2H_4I$ | 2.56% by weight (conversion ratio 97.7%) |
| $(C_6F_{13}C_2H_4O)_2SO_2$ | 9.17% by weight |

(Test 2)

Sulfation Step

In a 200 ml four-necked flask, 108.10 g fuming sulfuric acid containing 20% by weight of sulfur trioxide was supplied and 11.57 g $C_4F_9C_2H_4I$ was added dropwise over 40 minutes while stirring at room temperature without controlling the temperature, and then stirring was continued for one hour.

Hydrolysis Step

In a 500 ml four-necked flask, 231.91 g of a 1.5 wt % aqueous sodium sulfite solution was charged and the entire reactant (containing both an organic substance and an inorganic substance) obtained in the previous sulfation step was added dropwise over one hour at room temperature without controlling the temperature, and then the mixture was heated to 80° C. and maintained at the temperature for one hour. The reaction solution was allowed to stand, 7.34 g organic phase was fractionated. The organic phase was analyzed. The results are shown in the following table.

TABLE 2

| | |
|---|---|
| $C_4F_9C_2H_4OH$ | 98.23% by weight (yield 81.1%) |
| $C_4F_9C_2H_4I$ | 0.31% by weight (conversion ratio 99.7%) |
| $(C_4F_9C_2H_4O)_2SO_2$ | 1.35% by weight |

(Test 3)

Sulfation Step 0.91 g purified $(C_6F_{13}C_2H_4O)_2SO_2$ was charged in a 100 ml four-necked flask and 10.88 g fuming sulfuric acid containing 20% by weight of sulfur trioxide was added dropwise over 20 minutes while stirring at room temperature without controlling the temperature, and then the mixture was heated to 80° C. and continuously stirred for one hour.

Hydrolysis Step

In 100 ml four-necked flask, 20.10 g water was charged and the entire reactant (containing both an organic substance and an inorganic substance) obtained in the previous sulfation step was added dropwise over 30 minutes at room temperature without controlling the temperature, and then the mixture was heated to 80° C. and maintained at the temperature for one hour. The reaction solution was allowed to stand. 0.51 g organic phase was fractionated. The organic phase was analyzed. The results are shown in the following table.

TABLE 3

| | |
|---|---|
| $C_6F_{13}C_2H_4OH$ | 96.38% by weight (yield 70.3%) |
| $(C_6F_{13}C_2H_4O)_2SO_2$ | 3.23% by weight (conversion ratio 93.0%) |

(Test 4)

Sulfation Step

In a 200 ml four-necked flask, 59.68 g fuming sulfuric acid containing 20% by weight of sulfur trioxide was charged and 12.25 g mixture of $C_6F_{13}C_2H_4OH$ and $(C_6F_{13}C_2H_4O)_2SO_2$ (the concentration of $(C_6F_{13}C_2H_4O)_2SO_2$ was 22.78% by weight, and balance was $C_6F_{13}C_2H_4OH$) was added dropwise over 40 minutes at room temperature without controlling the temperature, and then the mixture was heated to 80° C. and continuously stirred for one hour.

Hydrolysis Step

In 500 ml four-necked flask, 150.41 g water was charged and the entire reactant (containing both an organic substance and an inorganic substance) obtained in the previous sulfation step was added dropwise over one hour at room temperature without controlling the temperature, and then the mixture was heated to 80° C. and maintained for one hour. The reaction solution was allowed to stand. 10.82 g organic phase was fractionated. The organic phase was analyzed. The results are shown in the following table.

TABLE 4

| | |
|---|---|
| $C_6F_{13}C_2H_4OH$ | 99.12% by weight (yield 89.2%) |
| $(C_6F_{13}C_2H_4O)_2SO_2$ | 0.59% by weight (conversion ratio 95.3%) |

(Test 5)

Sulfation Step

In a 200 ml four-necked flask, 21.61 g fuming sulfuric acid containing 20% by weight of sulfur trioxide was charged and 10.20 g mixture of $C_6F_{13}C_2H_4OH$(33.71 wt %), $C_6F_{13}C_2H_4I$ (52.85 wt %) and $(C_6F_{13}C_2H_4O)_2SO_2$ (13.44wt %) was added dropwise over 40 minutes at room temperature without controlling the temperature, and then the mixture was heated to 80° C. and continuously stirred for one hour.

Hydrolysis Step

In a 200 ml four-necked flask, 48.33 g of a 1.5 wt % aqueous sulfite solution was supplied and the entire reactant (containing both an organic substance and an inorganic substance) obtained in the previous sulfation step was added dropwise over one hour at room temperature without controlling the temperature, and then the mixture was heated to 80° C. and maintained for one hour. The reaction solution was allowed to stand. 7.55 g organic phase was fractionated. The organic phase was analyzed. The results are shown in the following table.

TABLE 5

| | |
|---|---|
| $C_6F_{13}C_2H_4OH$ | 88.84% by weight (yield 75.9%) |
| $C_6F_{13}C_2H_4I$ | 1.53% by weight (conversion ratio 97.0%) |
| $(C_6F_{13}C_2H_4O)_2SO_2$ | 9.63% by weight (conversion ratio 25.9%) |

Among the analytical results of Tests 1 to 5, a conversion ratio of 2-perfluoroalkylethyl iodide ($RfCH_2CH_2I$: $C_6F_{13}C_2H_4I$ in Tests 1 and 5, $C_4F_9C_2H_4I$ in Test 2) of Tests 1, 2 and 5 is an apparent value since the reaction of returning 2-perfluoroalkylethyl iodide (iodide) from bis(2-perfluoroalkylethyl)sulfate and the reaction for production of new bis(2-perfluoroalkylethyl)sulfate may occur.

The first sulfation step and the first hydrolysis step were carried out in Tests 1 and 2, while the second sulfation step and the second hydrolysis step were carried out in Tests 3 to 5.

Test 3 revealed that 2-perfluoroalkylethyl alcohol as the target substance can be obtained with a high purity by subjecting bis(2-perfluoroalkylethyl)sulfate to the sulfation reaction, followed by hydrolysis. As a result, it is understood that, in comparison with the case where only the first sulfation step and the first hydrolysis step were carried out, such as in Tests 1 and 2, 2-perfluoroalkylethyl alcohol can be obtained in a higher yield in the case where the second sulfation step and the second hydrolysis step are further conducted, such as in Test 3.

Test 4 revealed that, even when using bis(2-perfluoroalkylethyl)sulfate together with 2-perfluoroalkylethyl alcohol which is the target substance, a high conversion ratio of bis(2-perfluoroalkylethyl)sulfate and a high purity of 2-perfluoroalkylethyl alcohol, which are the same as those in the case of using bis(2-perfluoroalkylethyl)sulfate alone in Test 3, can be obtained and that neither production of by-products, nor reaction inhibition arises, both of which would cause a decrease in yield. Therefore, it is understood that, even when bis(2-perfluoroalkylethyl)sulfate is used together with 2-perfluoroalkylethyl alcohol which is the target substance in the second sulfation step, 2-perfluoroalkylethyl alcohol can be obtained in a higher yield.

Table 5 revealed that, when bis(2-perfluoroalkylethyl)sulfate is used together with not only 2-perfluoroalkylethyl alcohol as the target substance, but also 2-perfluoroalkylethyl iodide as a raw material, a conversion ratio of bis(2-perfluoroalkylethyl) is low even at the same reaction temperature and reaction time as those in Tests 3 and 4. As a result, it is understood that the yield can be effectively improved in the case where bis(2-perfluoroalkylethyl)sulfate produced in the first sulfation step is subjected to the second sulfation reaction step and the second hydrolysis step for obtaining 2-perfluoroalkylethyl alcohol after the first hydrolysis step, when compared with the case where the conversion of bis(2-perfluoroalkylethyl)sulfate is promoted by increasing the reaction temperature or prolonging the reaction time in the first sulfation step.

It should be noted that, since the yield of 2-perfluoroalkylethyl alcohol in each of Tests 4 and 5 is calculated based on not only those derived from bis(2-perfluoroalkylethyl)sulfate, but also those derived from others (2-perfluoroalkylethyl alcohol in Test 4, 2-perfluoroalkylethyl alcohol and 2-perfluoroalkylethyl iodide Test 5), the yield is apparently high. Therefore, when the results of Tests 3 to 5 are compared, attention should be paid to not the yield of 2-perfluoroalkylethyl alcohol, but to the conversion ratio of bis(2-perfluoroalkylethyl)sulfate.

(Supplementary Test)

By varying a molar ratio of sulfur trioxide in fuming sulfuric acid relative to 2-perfluoroalkylethyl iodide, an influence of the molar ratio on the proportions of 2-perfluoroalkylethyl alcohol and bis(2-perfluoroalkylethyl)sulfate was examined.

Sulfation Step

In a 200 ml four-necked flask, a predetermined amount of fuming sulfuric acid containing 20% by weight of sulfur trioxide was charged and 14.2 g (0.03 mol) $C_6F_{13}C_2H_4I$ was added dropwise over 40 minutes at room temperature without controlling the temperature, and then the mixture was continuously stirred for one hour. The amount of fuming sulfuric acid was adjusted so that the molar ratio of sulfur trioxide contained therein to $C_6F_{13}C_2H_4I$ is 3, 5, 7, 9 and 11.

Hydrolysis Step

In a 500 ml four-necked flask, 225 g of a 1.5 wt % aqueous sodium sulfite solution was charged and the entire reactant (containing an organic substance and an inorganic substance) obtained in the previous sulfation step was added dropwise over about one hour at room temperature without controlling the temperature, and then the mixture was heated to 80° C.

and maintained for one hour. The mixture was allowed to stand. An organic phase as a lower phase was fractionated.

Each organic phase thus obtained by varying the molar ratio of sulfur trioxide to $C_6F_{13}C_2H_4I$ (2-perfluoroalkylethyl iodide) was analyzed and the amounts (% by weight) of $C_6F_{13}C_2H_4OH$ (2-perfluoroalkylethyl alcohol) and $(C_6F_{13}C_2H_4O)_2SO_2$ (bis(2-perfluoroalkylethyl)sulfate) were determined. The results are shown in FIG. 3.

Figure 3:
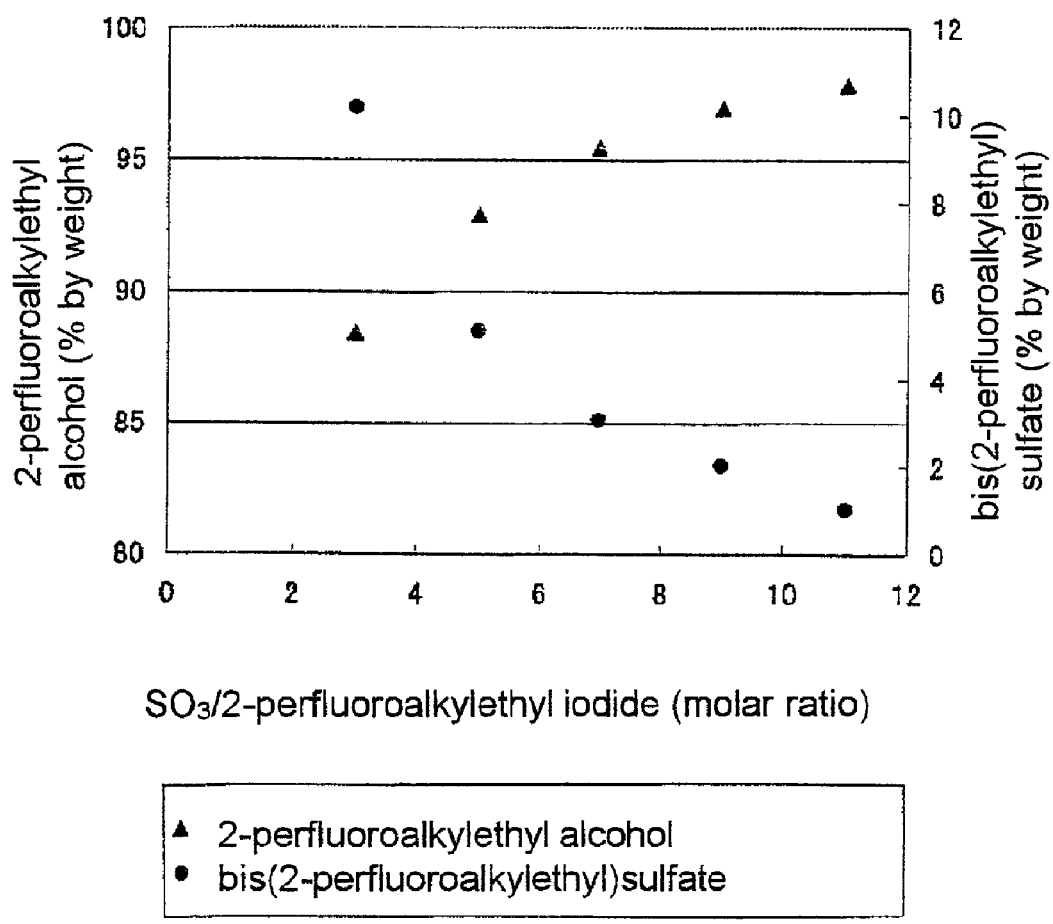
FIG. 3 is a graph showing influence of a molar ratio of sulfur trioxide in fuming sulfuric acid to 2-perfluoroalkylethyl iodide, on proportions of 2-perfluoroalkylethyl alcohol and bis(2-perfluoroalkylethyl)sulfate.

With reference to FIG. 3, it is understood that the proportion of bis(2-perfluoroalkylethyl)sulfate drastically decreases at a molar ratio $SO_3$ (sulfur trioxide)/2-perfluoroalkylethyl iodide of about 4, while the proportion of 2-perfluoroalkylethyl alcohol increases at the molar ratio. In a conventional production process, in order to minimize bis(2-perfluoroalkylethyl)sulfate contained in the final mixture, it was required to use fuming sulfuric acid, more specifically sulfur trioxide, in an excess amount with respect to 2-perfluoroalkylethyl iodide. For example, a molar ratio of sulfur trioxide to 2-perfluoroalkylethyl iodide in the range from 7 to 11 was required to be employed. In contrast, in the production process of the present invention, since bis(2-perfluoroalkylethyl) sulfate produced as a by-product in the first sulfation step is converted into 2-perfluoroalkylethyl sulfate in the second sulfation step and also 2-perfluoroalkylethyl sulfate can be converted into 2-perfluoroalkylethyl alcohol in the second hydrolysis step, it is not necessary to suppress the production of bis(2-perfluoroalkylethyl)sulfate as by-product in the first hydrolyses step. Therefore, according to the production process of the present invention, sulfur trioxide can be used at a molar ratio of 7 or less, for example, 3 or less to 2-perfluoroalkylethyl iodide in the first sulfation step. Even if the molar ratio is 1.5 mol or less in the first sulfation step, which corresponds to a stoichiometric ratio, a sufficiently high yield can be finally achieved.

What is claimed is:

1. A process for producing 2-perfluoroalkylethyl alcohol, which comprises:

a first sulfation step of bringing of bring 2-perfluoroalkylethyl iodide represented by the following formula:

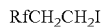

(wherein Rf is a linear perfluoroalkyl group having 1 to 10 carbon atoms, this definition of Rf is also applied to formulas below), into contact with fuming sulfuric acid to obtain a first sulfation reaction mixture comprising 2-perfluoroalkylethyl sulfate represented by the following formula:

$RfCH_2CH_2OSO_2OH$ and bis(2-perfluoroalkylethyl) sulfate as a by-product represented by the following formula:

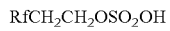

(wherein $Rf^1$ and $Rf^2$ are a linear perfluoroalkyl group having 1 to 10 carbon atoms which may be the same or different from each other, this definition of $Rf^1$ and $Rf^2$ is also applied to formulas below);

a first hydrolysis step of hydrolyzing 2-perfluoroalkylethyl sulfate produced in the first sulfation step to obtain a first hydrolysis reaction mixture comprising 2-perfluoroalkylethyl alcohol represented by the following formula:

a second sulfation step of bringing bis(2-perfluoroalkylethyl) sulfate produced in the first sulfation step into contact with fuming sulfuric acid to obtain a second sulfation reaction mixture comprising 2-perfluoroalkylethyl sulfate represented by the following formulas:

a second hydrolysis step of hydrolyzing 2-perfluoroalkylethyl sulfate produced in the second sulfation step to obtain a second hydrolysis reaction mixture comprising thus produced 2-perfluoroalkylethyl alcohol represented by the following formulas:

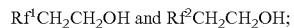

wherein the first and the second sulfation steps are separate steps from each other, and the first and the second hydrolysis steps are separate steps from each other.

2. The process according to claim 1, wherein
the first sulfation reaction mixture comprising 2-perfluoroalkylethyl sulfate and bis(2-perfluoroalkylethyl) sulfate is used in the first hydrolysis step to obtain the first hydrolysis reaction mixture comprising 2-perfluoroalkylethyl alcohol and bis(2-perfluoroalkylethyl) sulfate;
said first hydrolysis reaction mixture is used in the second sulfation step to obtain the second sulfation reaction mixture comprising 2-perfluoroalkylethyl alcohol and 2-perfluoroalkylethyl sulfate; and
the second sulfation reaction mixture is used in the second hydrolysis step to obtain the second hydrolysis reaction mixture comprising 2-perfluoroalkylethyl alcohol.

3. The process according to claim 1, wherein
the first sulfation reaction mixture comprising 2-perfluoroalkylethyl sulfate and bis(2-perfluoroalkylethyl) sulfate is used in the first hydrolysis step to obtain the first hydrolysis reaction mixture comprising 2-perfluoroalkylethyl alcohol and bis(2-perfluoroalkylethyl) sulfate;
said first hydrolysis reaction mixture is separated into a fraction of 2-perfluoroalkylethyl alcohol and a fraction of bis(2-perfluoroalkylethyl) sulfate;
thus separated fraction of bis(2-perfluoroalkylethyl) sulfate is used in the second sulfation step to obtain the second sulfation reaction mixture comprising 2-perfluoroalkylethyl sulfate; and
said second sulfation reaction mixture is used in the second hydrolysis step to obtain the second hydrolysis reaction mixture comprising 2-perfluoroalkylethyl alcohol.

4. The process according to claim 1, wherein the fuming sulfuric acid used in the first sulfation step comprises sulfur trioxide of which molar ratio is 2-perfluoroalkylethyl iodide is not greater than three.

5. The process according to claim 2, wherein the fuming sulfuric acid used in the first sulfation step comprises sulfur trioxide of which molar ratio is 2-perfluoroalkylethyl iodide is not greater than three.

6. The process according to claim 3, wherein the fuming sulfuric acid used in the first sulfation step comprises sulfur trioxide of which molar ratio is 2-perfluoroalkylethyl iodide is not greater than three.

* * * * *